US012723022B2

(12) United States Patent
Taulou et al.

(10) Patent No.: US 12,723,022 B2
(45) Date of Patent: Sep. 1, 2026

(54) METHOD FOR PRODUCING METHIONINE

(71) Applicants: ADISSEO FRANCE S.A.S., Antony (FR); CENTRE NATIONAL DE LA RECHERCHE SCIENTIFIQUE, Paris (FR); ECOLE SUPERIEURE DE CHIMIE, PHYSIQUE, ELECTRONIQUE DE LYON, Villeurbanne (FR); UNIVERSITE CLAUDE BERNARD LYON 1, Villeurbanne (FR)

(72) Inventors: Félix Taulou, Lyons (FR); Didier Morvan, Mornant (FR); Virginie Belliere-Baca, Millery (FR); Christophe Geantet, Miribel (FR)

(73) Assignees: ADISSEO FRANCE S.A.S., Antony (FR); CENTRE NATIONAL DE LA RECHERCHE SCIENTIFIQUE, Paris (FR); ECOLE SUPERIEURE DE CHIMIE PHYSIQUE ELECTRONIQUE DE LYON, Villeurbanne (FR); ELECTRONIQUE DE LYON UNIVERSITE CLAUDE BERNARD LYON 1, Villeurbanne (FR)

( * ) Notice: Subject to any disclaimer, the term of this patent is extended or adjusted under 35 U.S.C. 154(b) by 559 days.

(21) Appl. No.: 18/032,881

(22) PCT Filed: Oct. 20, 2021

(86) PCT No.: PCT/FR2021/051839

§ 371 (c)(1),
(2) Date: Apr. 20, 2023

(87) PCT Pub. No.: WO2022/084633

PCT Pub. Date: Apr. 28, 2022

(65) Prior Publication Data

US 2023/0391719 A1 Dec. 7, 2023

(30) Foreign Application Priority Data

Oct. 23, 2020 (FR) ..................................... 20/10881

(51) Int. Cl.
*C07C 323/58* (2006.01)
*C07C 391/00* (2006.01)

(52) U.S. Cl.
CPC .......... *C07C 323/58* (2013.01); *C07C 391/00* (2013.01)

(58) Field of Classification Search
USPC .......................................................... 562/556
See application file for complete search history.

(56) References Cited

U.S. PATENT DOCUMENTS

2017/0275247 A1 9/2017 Matsumura

FOREIGN PATENT DOCUMENTS

| | | | |
|---|---|---|---|
| CN | 113336684 | A | 9/2021 |
| EP | 3689851 | A1 | 8/2020 |
| JP | 393757 | A | 4/1991 |
| JP | H0393754 | A | 4/1991 |
| WO | 0160790 | A1 | 8/2001 |
| WO | 2004089863 | A1 | 10/2004 |
| WO | 2007034066 | A1 | 3/2007 |
| WO | 2020161067 | A1 | 8/2020 |
| WO | 2020161074 | A1 | 8/2020 |

OTHER PUBLICATIONS

Saudi Arabic Office Action for corresponding U.S. Appl. No. 18/032,881; Report dated Apr. 21, 2025.
International Search Report for corresponding application PCT/FR2021/051839 filed Oct. 20, 2021; Mail date Jan. 28, 2022.

*Primary Examiner* — Ana Z Muresan
(74) *Attorney, Agent, or Firm* — Oliff PLC

(57) ABSTRACT

The invention concerns a preparation of a compound of formula I,

[Chem 1]

$$CH_3XCH_2CH_2C(NH_2)COOH \quad (I)$$

where X represents S or Se,
by catalytic conversion of a compound of formula II

[Chem 2]

$$CH_3XCH_2CH_2C(Y)CN \quad (II)$$

where X represents S or Se and Y represents $NH_2$ or OH,
when Y represents $NH_2$, the conversion being carried out in the presence of water and of at least one catalyst comprising at least alumina, titanium dioxide or a mixture thereof, and
when Y represents OH, the conversion being carried out in the presence of water, of at least one catalyst comprising at least alumina, titanium dioxide, zirconia or a mixture thereof, and $NH_3$ or an ammonium salt.

17 Claims, No Drawings

METHOD FOR PRODUCING METHIONINE

TECHNICAL FIELD

The disclosure relates to an improvement of a method for producing methionine or its "seleniated" analogue (selenomethionine), from the precursors 2-amino-4-methylthiobutyronitrile or 2-hydroxy-4-methylthiobutyronitrile for methionine, or 2-amino-4-methylselenobutyronitrile or 2-hydroxy-4-methylselenobutyronitrile for selenomethionine.

BACKGROUND

The size of the methionine market no longer needs to be presented, particularly in animal nutrition, and its production methods are still the subject of numerous developments. The seleniated derivatives of methionine are also constituents of major interest in animal nutrition.

The preparation of methionine may be practiced by different methods involving various synthesis intermediates, and in particular 2-amino-4-methylthiobutyronitrile (AMTBN), 2-amino-4-methylthiobutyramide (AMTBM) and 2-hydroxy-4-methylthiobutyronitrile (HMTBN).

The document WO01/60790A1 describes a synthesis of methionine from 2-hydroxy-4-methylthiobutyronitrile (HMTBN). Upon reaction with ammonia, HMTBN is transformed into AMTBN which, in turn, is reacted with acetone in a basic medium to form AMTBM. A catalytic hydrolysis of AMTBM, in the presence of a titanium compound having a determined porosity, results in ammonium methioninate from which the methionine is recovered.

According to the document WO2004/089863A1, a method for producing the ammonium salt of HMTBA from the nitrile precursor of HMTBA is known, HMTBN, according to which HMTBN in aqueous solution, placed in the presence of a titanium-based catalyst, is converted in a single step into ammonium salt of HMTBA. This synthesis also leads to the formation of methionine and HMTBM, and the reported ammonium salt yields of HMTBA are in the range of 10%. They are too insufficient to consider an application of this method on an industrial scale.

SUMMARY AND DESCRIPTION

The present disclosure provides an alternative to the existing methods making it possible to dispense with at least one step, while leading to methionine or its seleniated derivative, in high yields.

It has been discovered according to the disclosure that the amino-nitrile (AMTBN or its seleniated equivalent) and hydroxy-nitrile (HMTBN or its seleniated equivalent) intermediates could be converted into methionine (or into selenomethionine) in a single step, in presence of water and a catalyst and, where appropriate, ammonia or an ammonium salt. The accessibility and performances of this conversion are such that its transposition to an industrial production of methionine is conceivable. Compared to the known synthetic methods and their improvements which remain insufficiently beneficial for conventional industrial methods to be modified, the present disclosure represents a real advance. Significant yields are obtained in very short times.

Thus, the disclosure provides a method for preparing a compound of formula (I),

[Chem 1]

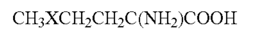

$CH_3XCH_2CH_2C(NH_2)COOH$ (I)

where X represents S or Se,
by catalytic conversion of a compound of formula (II)

[Chem 2]

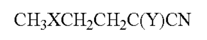

$CH_3XCH_2CH_2C(Y)CN$ (II)

where X represents S or Se and Y represents $NH_2$ or OH,
when Y represents $NH_2$, the conversion being carried out in the presence of water and of at least one catalyst comprising at least alumina, titanium dioxide or a mixture thereof, and where appropriate $NH_3$ or an ammonium salt, and
when Y represents OH, the conversion being carried out in the presence of water, of at least one catalyst comprising at least alumina, titanium dioxide, zirconia or a mixture thereof, and $NH_3$ or an ammonium salt.

By "where appropriate", it should be understood according to the disclosure that, when the method involves the hydroxy-nitrile precursor which is the compound of formula (II) in which Y represents OH, the presence of $NH_3$ or of an ammonium salt is necessary, while it is not necessary when the method involves the amino-nitrile precursor which is the compound of formula II in which Y represents $NH_2$. However, this definition does not exclude the presence of $NH_3$ when the method engages the amino-nitrile precursor, this variant constituting a particular implementation of the disclosure, described later on.

An ammonium salt according to the disclosure comprises any salt having the formula $(NH_4)_nA$ where A is in particular selected from halogens, carbonates, hydrogen carbonates, phosphates, hydrogen phosphates, sulfates, hydrogen sulfates, acetate, the citrate, formate, hydroxide and n is an integer varying from 1 to 5. As an illustration, it can be selected from $(NH_4)H_2PO_4$, $(NH_4)_2HPO_4$, $(NH_4)_3PO_4$, $(NH_4)HSO_4$, $(NH_4)_2SO_4$, $(NR_4)HCO_3$ or $(NH_4)_2CO_3$.

In the presence of such a catalyst above, the compound of formula (II) may be converted directly into methionine, while the methods known from the amino-nitrile compound or from the hydroxy-nitrile compound require passing through the corresponding amino-amide or hydroxy-nitrile intermediate, which is then hydrolyzed into methionine, each of the steps using different operating conditions.

In the present text, unless otherwise specified, the terms "compound (II) where Y is $NH_2$", "AMTBN" and "amino-nitrile" will be used interchangeably to denote 2-amino-4-methylthiobutyronitrile, and by analogy, the 2-amino-4-methylselenobutyronitrile. Likewise, the terms "compound (II) where Y is OH", "HMTBN" and "hydroxy-nitrile" refer to 2-hydroxy-4-methylthiobutyronitrile, and by analogy, to 2-hydroxy-4-methylselenobutyronitrile. By compound (II) it should be understood all these designations and therefore these two compounds, considered together or individually.

By "directly transformed", it should be understood that, when the method is performed on an industrial scale, the transformation may be carried out in one and the same reactor which comprises the catalyst, the reactor being supplied with a water mixture, compound (II) and optionally $NH_3$ or ammonium salt, or by each of the reactants separately, their mixing being performed in the reactor.

The term catalyst as used generally refers to the active phase of the catalyst, without excluding the fact that the catalyst may be doped and/or carried.

By alumina, titanium dioxide and zirconia, it should be understood all polymorphs, where applicable, of aluminum oxide $Al_2O_3$, titanium dioxide $TiO_2$ and zirconium dioxide $ZrO_2$, respectively, these forms being well known to those skilled in the art. The catalyst may also be a combination of two or even three of alumina, titanium dioxide and zirconia. It may also comprise any other entity promoting its catalytic function.

The features, applications and advantages of the disclosure are set out below in more detail, given that these features may be considered independently of one another, or in combination, irrespective of the combination.

According to the disclosure, the catalyst comprises or consists of one or several compound(s) selected from alumina, titanium dioxide and zirconia; it/they constitute(s) at least the active phase of the catalyst, optionally the carrier. Thus, if the catalyst does not consist entirely of one or more of said oxides, it may comprise any other compound that does not affect the performances of the catalyst, or even reinforces it. In a variant of the disclosure, the catalyst consists of one of said oxides.

The catalyst may be doped and/or carried. It may be doped with any element or compound conventionally used and well known to those skilled in the art. As an illustration, the doping of the catalyst may be performed by one or more of the elements and compounds selected from alkali metals, alkaline earth metals, lanthanum and any compound of the aforementioned elements. The following elements K, Cs, Sr, Ba and La are to be preferred. If the catalyst does not consist solely of alumina, titanium dioxide and/or zirconia, it may also be carried by any other compound conventionally used and well known to those skilled in the art, and in particular silica and silicoaluminates.

According to the disclosure, all of the solid catalysts mentioned above may be in powder form or preferably in the form of beads, extrudates, tablets, trilobes or any other form allowing it to be used in a reactor, preferably a fixed bed reactor or others or in batch mode in an open or pressurized reactor.

Said catalyst has advantageously a specific surface area of at least 10 $m^2/g$. Below this limit, the performances of the catalyst drop rapidly in particular with a decline in the selectivity for methionine in favor of that for AMBTM or HMTBM according to the compound (II), and a decrease in the conversion of the compound (II). This observation applies to the selenium equivalent. The upper limit of the specific surface area is not critical in the context of the disclosure, the latter being imposed by the active phases commercially available. The specific surface area values indicated in the present text are determined by the most common method, namely nitrogen physisorption and calculated by the BET method.

In a preferred implementation of the method of the disclosure, the catalyst is present in a concentration by mass comprised between 0.1% and 200% with respect to the mass of the compound (II), preferably between 0.5% and 100% and even better between 1% and 50%.

According to the disclosure, different equipment may be considered for performing the reaction in batch or continuously: the solid catalyst, whether doped or not, may be immobilized in a reactor in the form of grains or extrudates or any other form or carried on a metal foam. The reactor associated with this type of catalyst is preferably a fixed tubular or multi-tubular bed, operated in trickle mode or isothermal or adiabatic flooded mode, or an exchange reactor coated with catalyst.

The conversion of AMTBN or of HMTBN in the context of the disclosure is advantageously performed at a temperature ranging from 20° C. to 200° C., or even from 50° C. to 150° C., and even better from 80° C. to 110° C. It has been observed, over a reaction period ranging from about 10 minutes to 3 hours, that at a temperature lower than 20° C., the reaction is greatly slowed down, and that starting from 110° C., the more the temperature increases, the more selectivity for dinitrile and polypeptide of methionine rises to the detriment of that for methionine. Over the range from 80° C. to 110° C., it is observed that the selectivity for methionine is high.

In general, AMTBN or HMTBN is in an aqueous solution. This may have been prepared for the implementation of the method, or be derived from a reaction medium in which AMTBN or HMTBN has been produced, respectively. In this case, it is possible that AMTBN or HMTBN is not pure and includes traces, or even larger amounts, yet still negligible in that they do not adversely affect the conversion of AMTBN or HMTBN according to the disclosure.

The concentration of AMTBN or that of HMTBN, depending on the implemented transformation, may have an influence on the performances of the method, especially when it is too high. Thus, according to a variant of the disclosure, AMTBN is in aqueous solution in a concentration ranging from 0.01 M to 10 M, preferably from 0.05 M to 1 M, and even better from 0.2 M to 0.4 M. It has been noted that beyond 1 M, or even 0.8 M, if the conversion into AMTBN remains strong, the selectivity for methionine decreases while that for AMTBM, dinitrile and even polypeptide, respectively, rises.

When the production of methionine according to the disclosure involves HMTBN, ammonia should be added to the reaction medium. It is preferably present in a content varying from 1 equivalent to 50 equivalents with respect to HMTBN in ammonia. The ammonia may be brought to the medium by any technique, but advantageously, it is supplied in the form of continuous bubbling.

It has been observed that the presence of ammonia in the AMTBM solution before its conversion significantly improves the selectivity for methionine while decreasing the selectivity for dinitrile increasing over time in the absence of ammonia. The disclosure thus concerns an advantageous implementation of the method described above in which the AMTBN is placed in the presence of ammonia before being brought into contact with the catalyst, or even during the catalytic conversion within the reactor. Preferably, ammonia is introduced into the AMTBN solution by bubbling, possibly using an inert carrier gas, such as nitrogen.

The disclosure also concerns the continuous implementation of the method of the disclosure, and advantageously in the presence of ammonia, and even better of ammonia bubbling, in the AMTBN solution, before its conversion. According to this variant, the method is carried out under pressure comprised between 1 and 20 bar, preferably between 2 and 10 bar. Thus, the disclosure provides a device comprising a tank for the AMTBN solution and in which bubbling of a mixture of ammonia and nitrogen is provided. The AMTBN solution is pumped to a stainless-steel reactor which comprises the catalyst and which is heated by means of a sleeve to a temperature comprised between 80 to 100° C. The reaction medium is drawn to a gas/liquid separator from which the ammonia will be removed and from which the liquid will be processed to recover the methionine. The solution is then evaporated until a solid is obtained, then the solid is recrystallized in a water/ethanol mixture (1/6) at 60° C. The methionine thus obtained in the form of a white solid is washed, filtered and then dried. This continuous method described for obtaining methionine from AMTBN is equally applicable to obtaining methionine from HMTBN, yet the supply of ammonia remaining essential.

According to another aspect, there is provided a method for the controlled catalytic transformation of 2-amino-4-methylthiobutyronitrile or 2-amino-4-methylselenobutyronitrile into 2-amino-4-methylthiobutyramide or 2-amino-4-methylselenobutyramide, respectively, said conversion is performed in the presence of at least one catalyst comprising or consisting of alumina or titanium dioxide.

EXAMPLES

The disclosure and its advantages are illustrated in the examples below.

Example 1: Preparation of Methionine from AMTBN in the Presence of $TiO_2$, According to the Disclosure The hydrolysis reaction of AMTBN and the conditions under which it is carried out are described in the diagram below.

[Chem 3]

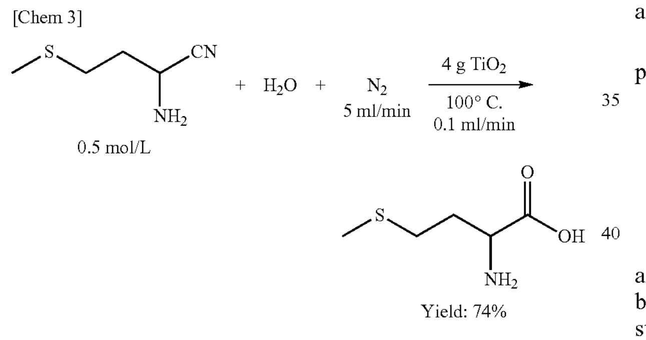

65 g of AMTBN are introduced with 1000 ml of $H_2O$ into a 1 liter screw-top vial. The solution is stirred at room temperature with a flow of nitrogen (5 ml/min), the solution is injected into a tubular reactor heated to 100° C. with a flow rate of 0.1 ml/min (contact time 10 minutes) and containing 4 grams of $TiO_2$ (anatase, 150 $m^2/g$, Norpro, ST 61120). The reaction is monitored over 48 hours by proton NMR.

The conversion of AMTBN is greater than 90%, the yield of methionine is on average 74% with an average selectivity of 81% and the yield of dinitrile is on average 11% with an average selectivity of 12%.

Example 2: Preparation of Methionine from AMTBN in the Presence of $TiO_2$ and Ammonia, According to the Disclosure—Influence of the Specific Surface Area of $TiO_2$ The hydrolysis reaction of AMTBN and the conditions under which it is carried out are described in the diagram below.

[Chem 4]

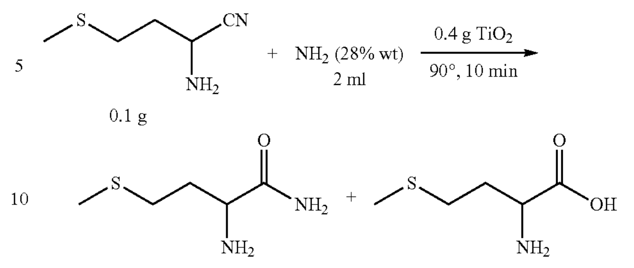

2.1 of $TiO_2$ (in the form of anatase) with a BET of 90 $m^2/g$ 0.4 g of $TiO_2$ (in the form of anatase) (90 $m^2/g$), then 0.1 g of AMTBN (98%) have been introduced with 2 ml of a solution of ammonia at 28 weight %. The solution has been heated at 90° C. for 10 minutes after which the solution has been filtered and analyzed by proton NMR.

The yield of methionine is 93%, that of AMTBM is 1% and that of dinitrile is 6%.

2.2 of $TiO_2$ (in the form of anatase) with a BET of 275 $m^2/g$ 0.4 g of $TiO_2$ (in the form of anatase) (275 $m^2/g$), then 0.1 g of AMTBN (98%) have been introduced with 2 ml of a solution of ammonia at 28 weight %. The solution has been heated at 90° C. for 10 minutes after which the solution has been filtered and analyzed by proton NMR.

The yield of methionine is 95%, that of AMTBM is 1% and that of dinitrile is 4%.

A $TiO_2$ catalyst having a BET of at least 90% should be preferred.

Example 3: Preparation of Methionine from AMTBN, in the Presence of Doped Titanium Dioxide and Ammonia, According to the Disclosure This example covers the use of $TiO_2$ doped with cesium and strontium, respectively. The doping has been performed by a method of impregnating $TiO_2$ with cesium hydroxide or strontium hydroxide, with a content of 4 weight % of cesium and strontium (non-metallic).

A solution of AMTBN at 0.8 mol/L is brought into contact with 5 g of either one of the doped catalysts for 10 minutes at a temperature of 100° C.

The results are presented in table 1 below.

TABLE 1

| Doping | AMTBN conversion | Selectivity for Met | Selectivity for AMTBM | Selectivity for dinitrile | Selectivity for others |
|---|---|---|---|---|---|
| Cs | 95% | 88% | 0% | 7% | 5% |
| Sr | 96% | 80% | 13% | 4% | 3% |

Example 4: Preparation of Methionine from AMTBN in the Presence of Titanium Dioxide and Ammonia According to a Continuous Method of the Disclosure The hydrolysis reaction of AMTBN and the conditions under which it is carried out are described in the diagram below.

[Chem 5]

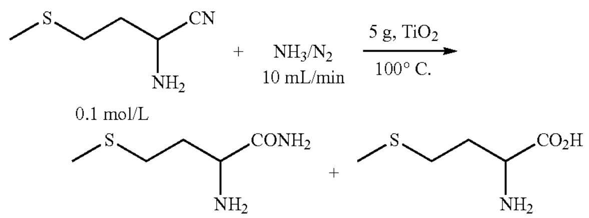

The catalyst is a titanium oxide having a specific surface area of 150 $m^2/g$.

5 g of this catalyst are placed in the reactor where a 0.1 mol/L aqueous solution of AMTBN is circulated with a flow rate of 0.2 ml/min, and an ammonia flow of 10 ml/min. The reaction temperature is 100° C. and the contact time is 6 minutes.

The results are presented in table 2 below.

TABLE 2

| monitoring period | Conversion of AMTBN | Selectivity for Met | Selectivity for AMTBM | Selectivity for dinitrile | Selectivity for others |
|---|---|---|---|---|---|
| 1 h | 94% | 88% | 5% | 3% | 4% |
| 4 h | 96% | 90% | 2% | 4% | 4% |

It is observed that the system is stable in conversion and in selectivity, with a high selectivity for methionine (90%), a very high conversion of AMTBN (96%) and a low selectivity for the other products. The yields of methionine and of AMTBM are respectively 86% and 2%.

Example 4: Preparation of Methionine from HMTBN, in the Presence of Titanium Dioxide and Di-Ammonium Hydrogen Phosphate, According to the Disclosure The hydrolysis reaction of HMTBN and the conditions under which it is carried out are described in the diagram below.

[Chem 6]

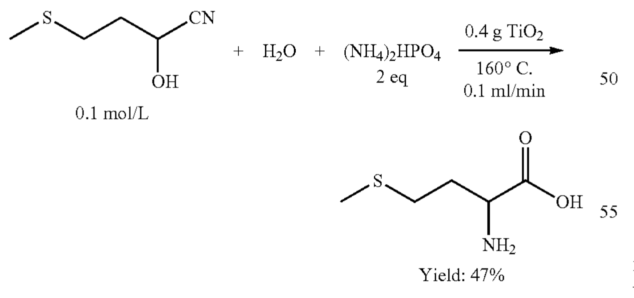

13.1 g of HMTBN are introduced with 1000 ml of $H_2O$ into a 1 liter screw-top vial. The solution is stirred at room temperature with a flow of nitrogen, the solution is injected into a tubular reactor heated to 160° C. with a flow rate of 0.1 ml/min (contact time 10 minutes) and containing 4 grams of $TiO_2$ (anatase, 150 $m^2/g$, Norpro, ST 61120). The reaction is monitored by HPLC, the yield of methionine is 47%.

Example 5: Preparation of Methionine from HMTBN, in the Presence of Titanium Dioxide and of Ammonia, According to the Disclosure The hydrolysis reaction of HMTBN and the conditions under which it is carried out are described in the diagram below.

[Chem 7]

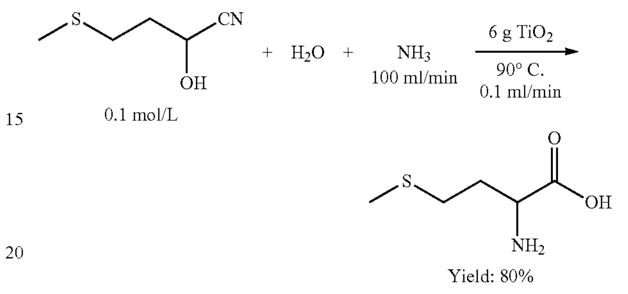

13.1 g of HMTBN are introduced with 1000 ml of $H_2O$ in a 1 liter screw-top vial. The solution is stirred at room temperature with a flow of ammonia having a flow rate of 100 ml/min, the solution is injected into a tubular reactor heated to 90° C. with a flow rate of 0.1 ml/min (contact time 15 minutes) and containing 6 grams of $TiO_2$ (anatase, 150 $m^2/g$, Norpro, ST 61120). The reaction is monitored by HPLC, the yield of methionine is 80%.

Example 6: Preparation of Methionine in the Presence of Titanium Dioxide, from HMTBN but without a Source of Ammonia, According to the Prior Art The hydrolysis reaction of HMTBN and the conditions under which it is carried out are described in the diagram below.

[Chem 8]

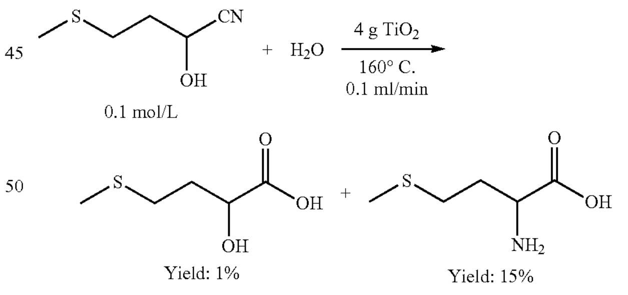

13.1 g of HMTBN are introduced with 1000 ml of $H_2O$ in 1 liter screw top vial. The solution is stirred at room temperature with a flow of nitrogen, the solution is injected into a tubular reactor heated to 160° C. with a flow rate of 0.1 ml/min (contact time 10 minutes) and containing 4 grams of $TiO_2$ (anatase, 150 $m^2/g$, Norpro, ST 61120). The reaction is monitored by HPLC, the yield of HMTBA is 1% and of methionine is 15%.

The comparison of the results of examples 4 to 5 according to the disclosure, with those obtained in a method carried out without ammonia or ammonium salt in example 6, demonstrates a considerable gain in the performance of the production of methionine in a method of disclosure. The same benefit is observed in the production of selenomethionine.

The invention claimed is:

1. A method for preparing a compound of formula I,

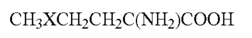

$$CH_3XCH_2CH_2C(NH_2)COOH \quad (I)$$

where X represents S or Se, wherein the method comprises the steps of (i) adding into a reactor at least one catalyst, the catalyst comprising at least alumina, titanium dioxide or a mixture thereof a compound of formula II

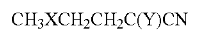

$$CH_3XCH_2CH_2C(Y)CN \quad (II)$$

where X represents S or Se and Y represents $NH_2$, water, and ammonia or a salt thereof, (ii) catalytically converting the compound of formula II the conversion is performed in a single step in the reactor; and (iii) then recovering the compound of formula I.

2. The method according to claim 1, wherein said catalyst is doped with one or more of the elements selected from the group consisting of alkali metals, alkaline earth metals, and lanthanum.

3. The method according to claim 1, wherein said catalyst has a BET specific surface area of at least 10 $m^2/g$.

4. The method according to claim 1, wherein the catalyst is in a mass concentration comprised between 0.1% and 200% with respect to the mass of the compound (II).

5. The method according to claim 1, wherein the compound of formula (II) is present in a concentration ranging from 0.01 M to 10 M.

6. The method according to claim 1, wherein the conversion is carried out at a temperature ranging from 20° C. to 200° C.

7. The method according to claim 1, wherein it is carried out continuously.

8. The method according to claim 1, wherein said catalyst is doped with one or more of the elements selected from the group consisting of K, Cs, Sr and Ba.

9. A method for preparing a compound of formula I,

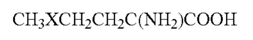

$$CH_3XCH_2CH_2C(NH_2)COOH \quad (I)$$

where X represents S or Se, wherein the method comprises the steps of catalytically converting a compound of formula II

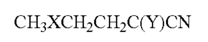

$$CH_3XCH_2CH_2C(Y)CN \quad (II)$$

where X represents S or Se and Y represents OH, the reaction medium comprises the compound of formula II, water, at least one catalyst and $NH_3$ or an ammonium salt, the conversion is performed in a single step, the catalyst comprises at least alumina, titanium dioxide, zirconia or a mixture thereof;

then recovering the compound of formula I.

10. The method according to claim 9, wherein said catalyst is doped with one or more of the elements selected from the group consisting of alkali metals, alkaline earth metals, and lanthanum.

11. The method according to claim 9, wherein said catalyst is doped with one or more of the elements selected from the group consisting of K, Cs, Sr and Ba.

12. The method according to claim 9, wherein said catalyst has a BET specific surface area of at least 10 $m^2/g$.

13. The method according to claim 9, wherein the catalyst is in a mass concentration comprised between 0.1% and 200% with respect to the mass of the compound (II).

14. The method according to claim 9, wherein the conversion is carried out at a temperature ranging from 20° C. to 200° C.

15. The method according to claim 9, wherein the ammonium salt is selected from the group consisting of $(NH_4)H_2PO_4$, $(NH_4)_2HPO_4$, $(NH_4)_3PO_4$, $(NH_4)HSO_4$, $(NH_4)_2SO_4$, $(NH_4)HCO_3$ and $(NH_4)_2CO_3$.

16. The method according to claim 9, wherein it is carried out continuously.

17. The method according to claim 9, comprising supplying the catalyst, water, compound (II) and $NH_3$ or ammonium salt in one and same reactor; mixing in the reactor and recovering compound (I) at the exit of the reactor.

* * * * *